United States Patent [19]

Arvidsson et al.

[11] Patent Number: 4,876,284

[45] Date of Patent: Oct. 24, 1989

[54] 1-ALKYL-2-AMINOTETRALIN DERIVATIVES

[75] Inventors: Folke L. E. Arvidsson, Uppsala; Per A. E. Carlsson, Gothenburg; Uli A. Hacksell, Uppsala; John S. M. Hjorth, Gothenborg; Anette M. Johansson, Uppsala; Per L. Lindberg, Askim, all of Sweden

[73] Assignee: Per Arvid Emil Carlsson, Gothenburg, Sweden

[21] Appl. No.: 143,260

[22] Filed: Jan. 11, 1988

Related U.S. Application Data

[63] Continuation of Ser. No. 16,447, Feb. 23, 1987, which is a continuation of Ser. No. 610,241, May 14, 1984, which is a continuation of Ser. No. 374,769, May 4, 1982, abandoned.

[30] Foreign Application Priority Data

May 8, 1981 [SE] Sweden ............................ 8102908

[51] Int. Cl.$^4$ ....................... C07C 87/64; C07C 87/28
[52] U.S. Cl. .................................. 514/657; 514/654; 564/374; 564/428
[58] Field of Search ............... 564/374, 428; 514/654, 514/657

[56] References Cited

U.S. PATENT DOCUMENTS 4,410,519 10/1983 Seiles et al. ................... 514/657

FOREIGN PATENT DOCUMENTS 2333847 1/1974 Fed. Rep. of Germany .
2752659 8/1978 Fed. Rep. of Germany .
2196158 3/1974 France .
1377356 12/1974 United Kingdom .

OTHER PUBLICATIONS

A. T. Dren et al., Local Anesthetic Activity and Acute Toxicity of N-Substituted 1,2,3,4-Tetrahydro-1- and 2-naphthylamines, Journal of Pharmaceutical Sciences, 67, 1978.

J. D. McDermed et al., Synthesis and Pharmacology of Some 2-Aminotetralins, Journal of Medicinal Chemistry, 18, 1975.

Mulder, A. H. et al., European Journal of Pharmacology, vol. 64, (1980), pp. 349-355.

Primary Examiner—Richard L. Raymond
Assistant Examiner—Kristina L. Konstas
Attorney, Agent, or Firm—Brumbaugh, Graves, Donohue & Raymond

[57] ABSTRACT

Compounds of the formula

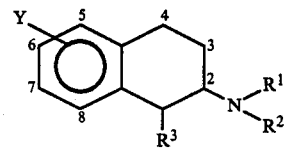

wherein $R^3$ and the $NR^1R^2$ group are in a cis-position to each other and wherein Y is OH, $R^4COO$, $(R^5)_2NCOO$ or $R^6O$ either in position 5 or position 7, whereby $R^4$ is an alkyl group having 1-5 carbon atoms or a possibly substituted phenyl group, $R^5$ is an alkyl group having 1-5 carbon atoms and $R^6$ is an allyl or benzyl group, $R^1$ is hydrogen or an alkyl group having 1-3 carbon atoms, $R^2$ is an alkyl group having 1-6 carbon atoms, a phenylalkyl- or m-hydroxyphenylalkyl group with 2-4 carbon atoms in the alkyl part, or an alkenyl group with 3-6 carbon atoms other than 1-alkenyl, and $R^3$ is an alkyl group having 1-3 carbon atoms, processes and intermediates for their preparation, pharmaceutical preparations and methods of treatment employing such compounds. The compounds are useful for therapeutic purposes, especially for treatment of disorders in the central nervous system.

25 Claims, No Drawings

1-ALKYL-2-AMINOTETRALIN DERIVATIVES

This application is a continuation of application Ser. No. 016,447, filed on 2/23/87. Which is a continuation of application Ser. No. 610,241 filed May 14, 1984, which in turn is a continuation in part of application Ser. No. 374,769 filed May 4, 1982 (now abandoned).

DESCRIPTION

1. Technical Field

The present invention is related to new 1,2,3,4-tetrahydro-2-naphtylamines, to processes for preparing such compounds, pharmaceutical preparations of such compounds and the use of such compounds in therapy.

An object of the invention is to provide compounds for therapeutic use, especially compounds having a therapeutic activity in the central nervous system.

2. Background Art

In UK Patent No. 1,377,356 (1974) tetralines of the formula

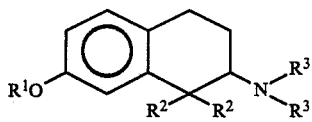

wherein $R^1$ is hydrogen or methyl, $R^2$ is alkyl having 1-6 carbon atoms, and $R^3$ is hydrogen or alkyl having 1-6 carbon atoms are described. Such compounds are stated to possess analgesic activity. 1,1-Dimethyl-2-(N,N-dimethylamino)-7-hydroxytetralin is mentioned as one example of a compound covered by the patent. Said compound is independently disclosed in CA 79: 146294b as having analgesic and intestinal movement accelerating actions.

In J. Pharm. Sci., 67, 880-82 (1978) a compound 1-methyl-2-(cyclopropylamino)-5-methoxytetralin is disclosed and said to possess local anesthetic activity.

Disclosure of Invention

According to the present invention it has been found that novel compounds of the formula

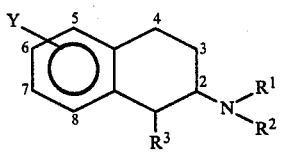

I wherein $R^3$ and the $NR^1R^2$ group are in a cis-position to each other and wherein Y is OH, $R^4$COO, $(R^5)_2$NCOO or $R^6$O either in position 5 or position 7, whereby $R^4$ is an alkyl group having 1-5 carbon atoms or a possibly substituted phenyl group, $R^5$ is an alkyl group having 1-5 carbon atoms and $R^6$ is an allyl or benzyl group, $R^1$ is hydrogen or an alkyl group having 1-3 carbon atoms, $R^2$ is an alkyl group having 1-6 carbon atoms, a phenylalkyl- or m-hydroxyphenylalkyl group with 2-4 carbon atoms in the alkyl part, or an alkenyl group with 3-6 carbon atoms other than 1-alkenyl, and $R^3$ is an alkyl group having 1-3 carbon atoms, as bases and pharmaceutically acceptable acid addition salts thereof, are potent neuropharmacological agents. Thus said compounds are active as presynaptic dopamine receptor agonists when administered to animals including man. The compounds are thus useful for treatment of disorders in the central nervous system, especially psychotic disorders in man.

The alkyl groups may be straight alkyl groups or branched alkyl groups.

A possibly substituted phenyl group $R^4$ may be a phenyl, 2,6-dimethylphenyl or 3- or 4-hydroxyphenyl group or a 3- or a 4-alkanoyloxyphenyl group with the formula

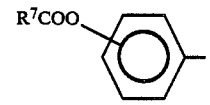

wherein $R^7$ is an alkyl group having 1-6 carbon atoms.

Symbols for numbers, atoms or groups referred to below have the boradest meaning previously assigned unless specified otherwise.

Both organic and inorganic acids can be employed to form non-toxic pharmaceutically acceptable acid addition salts of the compounds of this invention. Illustrative acids are sulfuric, nitric, phosphoric, hydrochloric, citric, acetic, lactic, tartaric, pamoic, ethanedisulfonic, sulfamic, succinic, cyclohexylsulfamic, fumaric, maleic and benzoic acid. These salts are readily prepared by methods known in the art.

In a restricted embodiment the invention is related to compounds of the formula I above wherein Y is OH, $R^4$COO, $(R^5)_2$NCOO and $R^6$O, whereby $R^4$ is a possibly substituted phenyl group, $R^5$ is $CH_3$ and $R^6$ is an allyl group, and $R^1$, $R^2$ and $R^3$ are as specified above. In a further restricted embodiment the invention is related to compounds of the formula I above, wherein Y is OH, $R^4$COO and $R^6$O, whereby $R^4$ is a possibly substituted phenyl group and $R^6$ is an allyl group, and $R^1$, $R^2$, and $R^3$ are as specified above. In a still further restricted embodiment the invention is related to compounds of the formula I above wherein Y is OH, $R^4$COO, $(R^5)_2$NCOO and $R^6$O wherein $R^4$ is methyl, phenyl, or 4-alkanoyloxyphenyl wherein the alkyl group has 1-4 carbon atoms, $R^5$ is methyl, $R^6$ is allyl, $R^1$ is hydrogen or alkyl having 1-3 carbon atoms, $R^2$ is alkyl having 3-6 carbon atoms or a phenylalkyl or m-hydroxyphenylalkyl group having an alkyl group with 2-3 carbon atoms, and $R^3$ is methyl or ethyl.

Preferred among the compounds of the formula I wherein Y represents $R^4$COO are those wherein $R^4$ is a 4-alkanoyloxyphenyl group wherein the alkyl group ($R^7$) has 4-6 carbon atoms.

According to a preferred embodiment the invention is related to compounds of the formula I wherein $R^1$ is n-$C_3H_7$.

Preferred compounds are those wherein $R^1$ is n-$C_3H_7$, $R^2$ is an alkyl group containing 3-6 carbon atoms or a phenylalkyl group with a straight alkyl group containing 2-3 carbon atoms and $R^3$ is $CH_3$ or $C_2H_5$. Further preferred are compounds wherein $R^1$ is n-$C_3H_7$, $R^2$ is an alkyl group with 3-5 carbon atoms and $R^3$ is $CH_3$.

In all the above defined groups of compounds, Y is either in 5-position or 7-position. Preferably Y is in 5-position.

Examples of compounds of the formula I according to the invention are given in the following Table, wherein Y is either in 5-position or 7-position.

| Y | R¹ | R² | R³ |
|---|---|---|---|
| OH | n-C$_3$H$_7$ | n-C$_3$H$_7$ | CH$_3$ |
| OH | n-C$_3$H$_7$ | n-C$_3$H$_7$ | C$_2$H$_5$ |
| OH | CH$_3$ | n-C$_3$H$_7$ | CH$_3$ |
| OH | H | n-C$_3$H$_7$ | CH$_3$ |
| OH | n-C$_3$H$_7$ | n-C$_4$H$_9$ | CH$_3$ |
| OH | n-C$_3$H$_7$ | n-C$_5$H$_{11}$ | CH$_3$ |
| OH | n-C$_3$H$_7$ | —CH$_2$-CH(CH$_3$)$_2$ | CH$_3$ |
| OH | n-C$_3$H$_7$ | —(CH$_2$)$_2$—C$_6$H$_4$—OH | CH$_3$ |
| OH | n-C$_3$H$_7$ | —(CH$_2$)$_3$—C$_6$H$_5$ | CH$_3$ |
| OH | n-C$_3$H$_7$ | —CH$_2$—CH=CH$_2$ | CH$_3$ |
| OCCH$_3$ (O=) | n-C$_3$H$_7$ | n-C$_3$H$_7$ | CH$_3$ |
| OC(=O)—C$_6$H$_5$ | n-C$_3$H$_7$ | n-C$_3$H$_7$ | CH$_3$ |
| OC(=O)—C$_6$H$_4$—OCC(CH$_3$)$_3$(=O) | n-C$_3$H$_7$ | n-C$_3$H$_7$ | CH$_3$ |
| OCH$_2$CH=CH$_2$ | n-C$_3$H$_7$ | n-C$_3$H$_7$ | CH$_3$ |
| OCN(CH$_3$)$_2$ (O=) | n-C$_3$H$_7$ | n-C$_3$H$_7$ | CH$_3$ |
| OH | n-C$_3$H$_7$ | —(CH$_2$)$_2$—C$_6$H$_5$ | CH$_3$ |
| OH | n-C$_3$H$_7$ | n-C$_3$H$_7$ | N—C$_3$H$_7$ |

The compounds of formula I contain two asymmetric carbon atoms (C$_1$ and C$_2$) giving cis/trans isomerism.

The therapeutic properties of the compounds is ascribed only to the cis-configuration, but may to a greater or lesser degree be ascribed to either or both of the two enantiomers occurring. Thus the pure enantiomers as well as mixtures thereof are within the scope of the invention.

The invention takes into consideration that compounds which structurally deviate from the formula I, after administration to a living organism may be transformed to a compound of the formula I and in this structural form exert their effects. This consideration is a further aspect of the invention. Likewise, certain compounds of formula I may be metabolized into other compounds of formula I before exerting their effect. Compounds of the invention wherein Y is R$^4$COO, (R$^5$)$_2$NCOO or R$^6$O are thus believed to exert their main activity after metabolism to compounds wherein Y is OH.

Methods of Preparation

The compounds of the invention may be obtained by one of the following methods constituting a further aspect of the invention. The formulas II–XI for the intermediates only include, where applicable, the cis-configurations unless something else is stated.

(a) An ether or ester of the formula $$RO-\text{(tetrahydronaphthalene)}-N(R^1)(R^2), R^3 \qquad II$$

with RO in position 5 or 7 and wherein R represents a hydrocarbon or acyl residue, preferably an alkyl group having 1–5 carbon atoms or a benzyl group, or an alkylcarbonyl group having 2–6 carbon atoms, and R$^1$, R$^2$ and R$^3$ are as defined above, may be cleaved to form a compound of formula I wherein Y is a hydroxy group.

When R is a hydrocarbon residue the cleavage may be carried out by treating the compound of formula II with an acidic nucleophilic reagent such as aqueous HBr, or HI, HBr/CH$_3$COOH, BBr$_3$, AlCl$_3$, pyridine-HCl or (CH$_3$)$_3$SiI, or with a basic nucleophilic reagent such as CH$_3$C$_6$H$_4$-S$^\ominus$ or C$_2$H$_5$-S$^\ominus$. When R is a benzyl group the cleavage may also be carried out by reduction, preferably with hydrogen using Pd or PtO₂ as catalyst.

When R is an acyl residue the cleavage may be carried out by hydrolysis in an aqueous acid or base or by reduction, preferably by LiAlH₄.

The compound of formula II is obtainable by first alkylating a compound of formula II A, A pure enantiomer of compound II may be prepared by first conversion of IID (cis) into the (-)-O-methyl-mandelic acid amide IIE followed by chromatographic separation of the two diastereomers and cleavage by subsequent reaction with potassium tert-butoxide in tetrahydrofuran with traces of water and CH₃Li, and then the desired of the two enantiomers (IID' and IID")

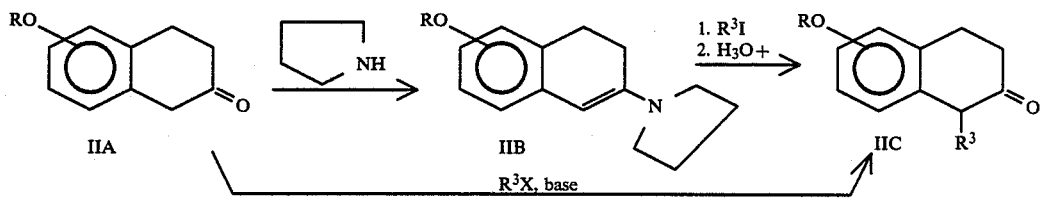

wherein R (in position 5 or 7) is a hydrocarbon or an acyl residue, either via the enamine (IIB) route or by direct alkylation of the ketone IIA under basic conditions, to the formation of a compound of formula IIC, then converting compound IIC into a compound of the formula IID by reductive alkylation with R¹NH₂ and H₂/PtO₂ followed by isomeric separation of the cis- and trans-isomers formed, then if desired is alkylated.

b) A compound of formula III

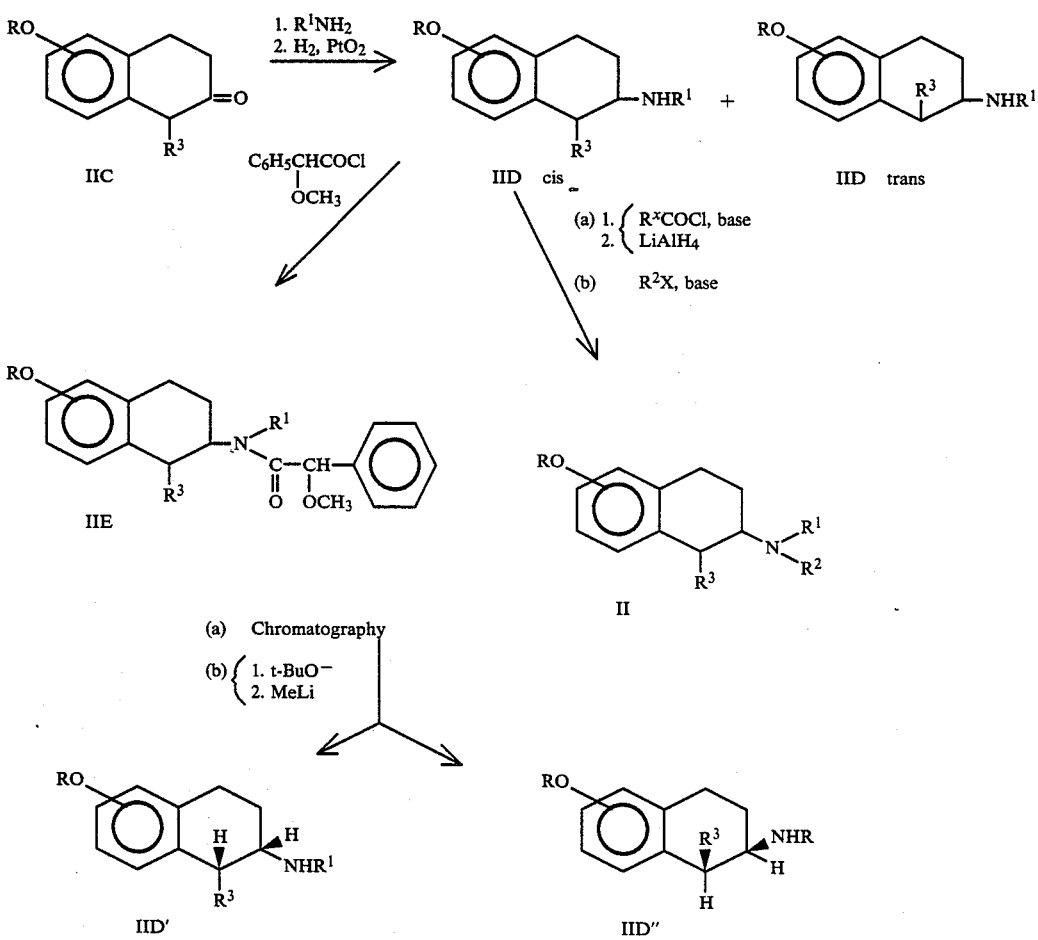

alkylating the cis isomer with formula IID by acylation with RˣCOCl, wherein Rˣ is an alkyl group defined by the relation Rˣ-CH₂ equals R², followed by LiAlH₄ reduction, or alternatively by a direct alkylation with R²X (X=Cl, Br, I) in the presence of a base.

wherein Y (in position 5 or 7) is OH, R¹ is other than hydrogen and R² is other than m-hydroxyphenylalkyl may be converted into a compound of the formula I wherein Y is R⁴COO, (R⁵)₂NCOO or R⁶O by treating the first mentioned compound with an appropriate carboxylic acid halide R⁴COX or anhydride (R⁴CO)₂O or with an appropriate carbamoyl halide (R⁵)₂NCOX in the presence of a base such as triethylamine or pyridine or an acid such as H₂SO₄ or CF₃COOH or with an appropriate allyl or benzyl halide R⁶X in the presence of a base such as triethylamine, pyridine or potassium t-butoxide. X represents a halogen, preferably Cl or Br.

Alternatively, when conversion of Y=OH into R⁴COO is intended and R⁴ is

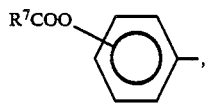

a compound of formula I wherein Y is OH may first be converted to a compound of formula I wherein Y is

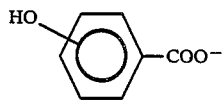

which is then treated with an appropriate carboxylic acid halide R⁷COX or anhydride (R⁷CO)₂O in the presence of a base or an acid.

(c) A compound of the formula

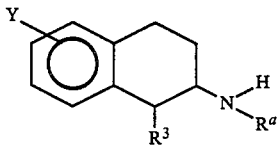

wherein R$^a$ is either R¹ or R², and R¹, R², R³ and Y (in positions 5 or 7) are as defined above, may be converted into a compound of formula I by alkylation of the nitrogen atom with an appropriate alkylating agent. Thus, the starting compound wherein R$^a$ is R¹ may be treated with an alkyl, alkenyl, phenylalkyl- or m-hydroxyphenylalkyl halide or tosylate R²X¹, wherein X¹ represents Cl, Br, I or

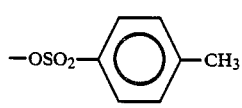

in an organic solvent such as acetonitrile or acetone and in the presence of a base such as K₂CO₃ or NaOH, or said starting compound may be treated with a carboxylic acid NaBH₄ complex R$^b$COOH—NaBH₄, wherein R$^b$ is defined by the relation R$^b$—CH₂—equals R². To the formation of a compound of formula I wherein at least one of R¹ and R² is CH₃, the alkylation reaction may be carried out by treatment of the compound of formula IV with a formaldyhyde —Na(CN)BH₃ mixture, or with formaldehyde and formic acid.

(d) An amide of the formula

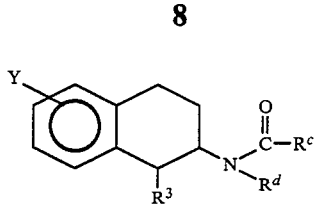

wherein Y (in position 5 or 7) is OH or R⁶O, and R⁶ is as defined above, R$^c$ is an alkyl group defined by the relation R$^c$—CH₂—equals either R¹ or R² and R$^d$ is the other of R¹ and R², may be reduced, e.g. by treatment with a hydride reducing agent such as LiAlH₄ in ether or tetrahydrofuran or BH₃ in tetrahydrofuran, to the formation of a compound of formula I.

(e) An enamine with either a C₁-C₂ or a C₂-C₃ double bond or an imine base (without R¹) or immonium salt (e.g. ClO₄⁻ or BF₄⁻) with a C₂-N double bond of the formula

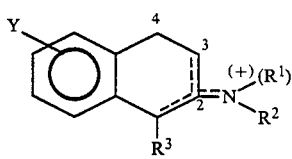

wherein Y (in position 5 or 7) is other than allyloxy, R² is other than alkenyl and R¹ and R³ are as defined above may be reduced to a compound of formula I, preferably by catalytic hydrogenation using PtO₂ or Pd as a catalyst. The product, which contains both cis and trans isomers, must be subjected to isomeric separation, preferably by fractional crystallization or chromatographic separation. If Y in the starting material is benzyloxy, this is hydrogenolysed to OH.

(f) An alkene of the formula

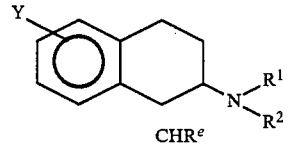

wherein R$^e$ is CH₃ or C₂H₅, Y (in position 5 or 7) is other than allyloxy, R² is other than alkenyl and R¹ is as defined above may be reduced, preferably by catalytic hydrogenation using PtO₂ or Pd as a catalyst, to a compound of formula I wherein R³ is C₂H₅ or n-C₃H₇. The product which contains both cis and trans isomers must undergo isomeric separation, preferably by fractional crystallization or chromatographic separation. If Y in the starting material is benzyloxy this is hydrogenolysed to OH.

(g) A compound of the formula

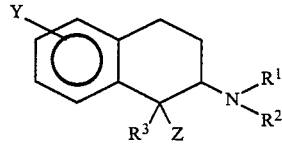

in the form of its cis and/or trans-configuration, wherein Z is a group sensitive to hydrogenolysis such as OH and halogen, Y (in position 5 or 7) is other than allyloxy, R² is other than alkenyl and R¹ and R³ are as defined above may be reduced, preferably by catalytic hydrogenation using PtO₂ or Pd as a catalyst, to a compound of formula I. The product which contains both cis and trans isomers must undergo isomeric separation. If Y in the starting material is benzyloxy this is hydrogenolysed to OH.

(h) A compound of the formula

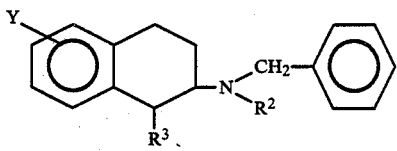  IX wherein Y (in position 5 or 7) is other than allyloxy, $R^2$ is other than alkenyl and $R^3$ is as defined above may be catalytically hydrogenated, preferably by using PtO₂ or Pd as a catalyst, to a compound of formula I wherein $R^1$ is hydrogen. If Y in the starting material is benzyloxy this is converted to OH.

(i) A compound of the formula

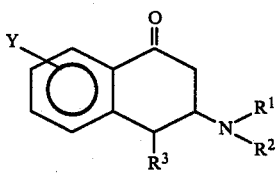  X wherein Y (in position 5 or 7) is other than allyloxy, $R^2$ is other than alkenyl and $R^1$ and $R^3$ are as defined above may be converted to a compound of formula I by reduction of the keto function, either by direct conversion to CH₂ with e.g. hydrazine under alkaline conditions, or by a two-step reduction, with e.g. catalytic hydrogenation, which may involve an intermediary formation of a C₃-C₄ double bond or a conversion of the intermediary formed 4-OH group into another group such as halogen. If Y in the starting material is benzyloxy this may at the same time be converted to OH.

(j) in a compound of the formula

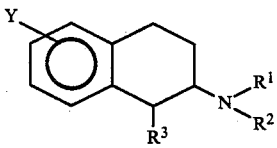  XI wherein X (in position 5 or 7) represents SO₃H, Cl or NH₂, a hydroxy group may be substituted for the group X to the formation of a compound of formula I wherein Y represents a hydroxy group. When X is SO₃H or Cl said reaction may be carried out by treatment with a strong alkali under heating, suitably with an alkali melt such as KOH when X is SO₃H, and with a strong aqueous alkali such as NaOH or KOH when X is Cl. When X is NH₂ the reaction may be carried out by treatment with aqueous nitrous acid to the formation of an intermediate diazonium compound which is then subjected to hydrolysis in water.

(k) a racemic mixture or a mixture partly enriched on one of the enantiomers of a compound of formula

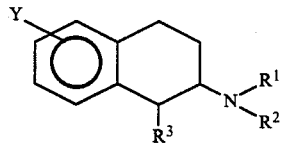  I may be subjected to enantiomeric separation to obtain a pure enantiomer of compound I. This may be done by methods known in the art. These methods include recrystallization of diastereomeric salts with pure enantiomers of acids such as tartaric acid, 0.0-dibenzoyltartaric acid, mandelic acid and camphor-10-sulphonic acid.

Free bases formed in any of the above methods a) - k) may subsequently be converted into their acid addition salts, and acid addition salts formed may subsequently be converted into the corresponding bases or other acid addition salts.

Intermediates

Some of the intermediates or starting materials mentioned above and the preparation thereof are known. However, certain intermediates or starting materials are novel and constitute a further aspect of the invention. Thus, in one aspect the invention is related to novel compounds of the formula

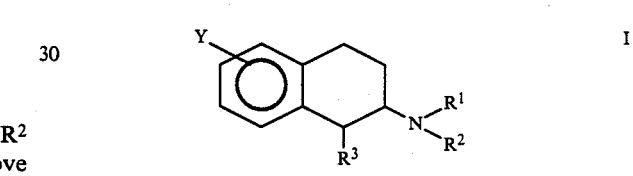  I wherein $Y^1$ is an alkoxy group containing 1-5 carbon atoms or a benzyloxy group and $R^1$, $R^2$ and $R^3$ are as described above as well as to acid addition salts of said compounds, and to the method for preparing said compounds or salts.

Pharmaceutical Preparations

Pharmaceutical preparations of the compounds of the invention constitute a further aspect of the invention.

In clinical practice the compounds of the present invention will normally be administered orally, rectally, or by injection, in the form of pharmaceutical preparations comprising the active ingredient either as a free base or as a pharmaceutically acceptable non-toxic, acid addition salt, e.g. the hydrochloride, lactate, acetate, sulfamate, and the like, in association with a pharmaceutically acceptable carrier.

Accordingly, terms relating to the novel compounds of this invention, whether generically or specifically, are intended to include both the free amine base and the acid addition salts of the free base, unless the context in which such terms are used, e.g. in the specific examples, would be inconsistent with the broad concept. The carrier may be a solid, semisolid or liquid diluent or capsule. These pharmaceutical preparations constitute a further aspect of this invention. Usually the active substance will constitute between 0.1 and 99% by weight of the preparation, more specifically between 0.5 and 20% by weight for preparation intended for injection and between 0.2 and 95% by weight for preparations suitable for oral administration.

Pharmaceutical preparations containing a compound of the invention in a solid form of dosage units for oral application may preferably contain between 2 and 95% by weight of the active substance, in such preparations the selected compound may be mixed with a solid fine grain carrier, e.g. lactose, saccharose, sorbitol, mannitol, starches such as potato starch, corn starch or amylopectin, cellulose derivatives, or gelatin and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g. gum arabic, gelatin, talcum, titanium dioxide, and the like. Alternatively the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatin capsules (pearl-shaped closed capsules) consisting of gelatin and, for example, glycerol, or similar closed capsules, the active substance may be admixed with a vegetable oil. Hard gelatin capsules may contain granulates of the active substance in combination with solid, fine grain carriers such as lactose, saccharose, sorbitol, mannitol, starches (e.g. potato starch, corn starch or amylopectin), cellulose derivatives or gelatin. Liquid preparations for oral application may be in the form of syrups or suspensions, for example, solutions containing from about 0.2% to about 20% by weight of the active substance herein described, the balance being sugar and a mixture of ethanol, water, glycerol and propyleneglycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in an concentration of from about 0.5% to about 10% by weight. These solutions may also contain stabilizing agents and/or buffering agents and may conveniently be provided in various dosage unit ampoules.

In therapeutical treatment the suitable daily doses of the compounds of the invention are 100–5000 mg for oral application, preferentially 500–3000 mg, and 0.5–500 mg for parenteral application, preferentially 25–250 mg.

Working Examples

The following examples will further illustrate the invention.

Preparation of Intermediates

Example I 1.
cis-5-Methoxy-1-methyl-2-(n-propylamino)tetralin

To a solution of 5-metoxy-1-methyl-2-tetralone (2.0 g, 10.5 mmol) in absolute EtOH (50 ml) were added acetic acid (1.9 g, 31.5 mmol), n-propylamine (1.85 g, 31.5 mmol) and 4 A molecular sieves. The mixture was heated in a closed flask at 80° C. for 1 hour. The molecular sieves were filtered off and the solution was hydrogenated ($PtO_2$) at atmospheric pressure. The catalyst was filtered off (Celite) and the volatiles were evaporated. Dilute HCl (50 ml) was added to the solid residue. The resulting acidic solution was washed with ether, alkanilized with 5% NaOH and extracted twice with ether. The ether extracts were combined, dried ($K_2CO_3$) and evaporated. The resulting crude base was eluted through an alumina column with ether-light petroleum (1:4) as eluant, affording an oil of 71% isomeric purity (GC). The hydrochloride was prepared and recrystallized three times from MeOH-ether. Yield 500 mg (17%) of cis-5-methoxy-1-methyl-2-(propylamino)-tetralin. HCl, mp 225°–230° C.; GC (225° C.) isomeric purity >95%, retention time 1.6 min; NMR (MeOH-$d_4$) $\delta 1.06$ (s,3H), $\delta 1.24$ (d,3H), $\delta 1.68$–3.58 (m, 10H), $\delta 3.80$ (s,3H), $\delta 6.71$–6.81 (m,2H), $\delta 7.07$–7.20 (m,1H); MS (70 eV) m/z 233 (57%), 204 (52%), 175 (62%).

Example I2.
cis-5-Methoxy-1-methyl-2-(di-n-propylamino) tetralin hydrochloride

Propionyl chloride (0.49 g, 5.2 mmol) in dry ether (10 ml) was added to a solution of cis-5-methoxy-1-methyl-2-(n-propylamino)tetralin (350 mg, 1.5 mmol) and triethylamine (0.49 g, 4.9 mmol) in dry ether (80 ml). After 30 min. at room temperature the reaction mixture was filtered and the ether was evaporated. The resulting crude amide was passed through an alumina column eluted with ether. The purified amide dissolved in dry THF (20 ml) was added to a suspension of $LiAlH_4$ (1.0 g, 26 mmol) in dry THF (30 ml) under $N_2$. After stirring under reflux for 3 h, the reaction mixture was hydrolyzed, the precipitate was filtered off and the solvent was evaporated. The oily residue was chromatographed on an alumina column with ether-light petroleum (1:1) as eluant. The hydrochloride was prepared and recrystallized from EtOH-ether to give 200 mg (42%) of title product: mp 170.5°–171.5° C.; GC (215° C.) isomeric purity >95%, retention time 2.45 min; NMR (MeOH-$d_4$) $\delta 1.05$ (t,6H) $\delta 1.32$ (d,3H) $\delta 1.64$–3.66 (m,14H), $\delta 3.80$ (s,3H), $\delta 6.71$–6.82 (m,2H), $\delta 7.10$–7.20 (m,1H); MS (70 eV) m/z 275 (28%), 246 (100%), 176 (69%).

Example I 3. (+)-and (-)-cis-5-Methoxy-1-methyl-2-(di-n-propylamino)tetralin hydrochloride (−)-cis-5-Methoxy-1-methyl-2-(di-n-propylamino)-tetralin hydrochloride. R-(-)-O-Methylmandelic acid chloride (4.1 g, 0.022 mol), prepared from R-(-)-O-methylmandelic acid by treatment with thionylchloride at 20° C. for 10 hours, dissolved in $CH_2Cl_2$ (5 ml) was added at room temperature to a stirred mixture of (±)-cis-5-methoxy-1-methyl-2-(n-propylamino)tetralin (3.0 g, 0.013 mol), $CH_2Cl_2$ (25 ml), $H_2O$ (25 ml) and 5% aqueous NaOH (12 ml). After stirring for 1.5 hour the phases were separated and the organic phase was washed once with water then dried ($MgSO_4$), filtered and evaporated. Ether (15 ml) was added to the residue and one of the diastereomeric amides precipitated (1.2 g). The precipitate was collected by filtration and then recrystallized from acetone to give 1.0 g of one of the diastereomers. The filtrates from the treatment with ether and acetone were combined and evaporated. This oily residue was chromatographed on a $SiO2$ column with ether/light petroleum (50:50) as eluant. The fractions containing that one of the diastereomers, which is eluated first were combined and the solvent was evaporated to give 0.6 g of one of the diastereomeric amides. This diastereomer showed to be the same diastereomeric amide (TLC) as was isolated by precipitation from ether (see above). Total yield 1.6 g. (Stereoisomerically pure according to GLC (capillary column SE-54)). This diastereomeric amide (1.6 g, 0.0041 mol) was dissolved in dry tetrahydrofuran (40 ml) and kept at −8° C. under nitrogen. To this solution was added potassium-tert-butoxide (21.1 g, 0.19 mol) and water (0.60 ml, 0.035 mol) with the addition divided in seven portions over 12 days. 13 days after the first addition of reagents ice, water and ether was added to the reaction mixture until two layers formed. The phases were separated and the organic layer was washed with 1M HCl, saturated aqueous Na$_2$CO$_3$, dried (MgSO$_4$), filtered and evaporated. The residue, dissolved in ether/light petroleum (50:50), was passed through a SiO$_2$ column and eluated first with ether-light petroleum (50:50) and then with ether, yielding a solid (0.56 g) after evaporation. To this solid (0.56 g, 0.0022 mol) dissolved in dry tetrahydrofuran (40 ml) at −8° C. and under nitrogen, CH$_3$Li (0.0054 mol) was added under stirring. The mixture was stirred for 10 min. then extracted with saturated aqueous NH$_4$Cl. The phases were separated and the organic layer was extracted with 5M HCl. The combined aqueous layers were alkalinized with 5M NaOH and extracted with ether. The organic layer was dried (K$_2$C$_3$) and filtered. HCl-saturated ether was added giving a precipitate which was recrystallized giving (−)-cis-5-methoxy-1-methyl-2-(n-propylamino)tetralin hydrochloride. (0.42 g, 37% total yield of the maximal theoretical), m.p. 269°-270° C. decomp.; $[\alpha]_D^{22} = -53.2$ (c=1.1, CH$_3$OH).

Propionylchloride (0.28 g, 0.0030 mol) in dry ether (5 ml) was slowly added at 5° C. to a solution of (-)-cis-5-methoxy-1-methyl-2-(n-propylamino)tetralin (0.35 g, 0.0015 mol), triethylamine (0.31 g, 0.0030 mol) and dry ether (45 ml). The mixture was stirred at room temperature for 1 hour. whereupon the triethylammoniumchloride formed was filtered off and the solvent evaporated. The residue (0.40 g) dissolved in dry tetrahydrofuran (10 ml) was added to a suspension of LiAlH$_4$ (0.80 g, 0.021 mol) in dry tetrahydrofuran (40 ml) under nitrogen. After stirring under reflux for 5 hours, the mixture was hydrolyzed, the precipitate was filtered off, and the solvent was evaporated. The residue was passed through an alumina column with ether/light petroleum (20:80) as eluant, and the amine was precipitated as the hydrochloride and recrystallized from ethanol-ether to give (−)-cis-5-methoxy-1-methyl-2-(di-n-propylamino)tetralin hydrochloride. (0.37 g, 79%) m.p. 161°-162° C. $[\alpha]_D^{22} = -48.2$ (c=1.1, CH$_3$OH).

(+)-cis-5-Methoxy-1-methyl-2-(di-n-propylamino)tetralin hydrochloride. The latter fractions, from the separation of the diastereomeric (−)-R-O-methylmandelamides on SiO$_2$ with ether/light petroleum (50:50) as eluant (see above) containing the other diastereomeric amide, were combined and evaporated. The oily residue (2.0g, 0.0052mol) was treated with potassium-tert-butoxide (27.16 g, 0.24 mol) and H$_2$O (0.76 ml, 0.042 mol) in dry tetrahydrofuran and then with CH$_3$Li (0.0029 mol) in dry tetrahydrofuran, as described above, to give (+)-cis-5-methoxy-1-methyl-2-(n-propylamino)tetralin hydrochloride (0.36 g, 25%) m.p. 275°-276° decomp.

$[\alpha]_D^{22} = +51.1$ (c=1.1, CH$_3$OH)

(+)-cis-5-Methoxy-1-methyl-2-(n-propylamino)tetralin (0.30 g, 0.0013 mol) was treated with propionyl chloride (0.23 g, 0.0025 mol) and triethylamine (0.26 g, 0.0026 mol) in dry ether and then with LiAlH$_4$ (0.60 g, 0.016 mol) in dry tetrahydrofuran, (see above) giving (+)-cis-5-methoxy-1-methyl-2-(di-n-propylamino) tetralin hydrochloride (0.29 g, 72%) m.p. 160°-161° C.. $[\alpha]_D^{22} = +46.8$ (c=0.9; CH$_3$OH)

Examle I4

(±)-cis-7-methoxy-1-methyl-2-(n-propylamino)tetralin (1)

To a solution of 7-methoxy-1-methyl-2-tetralone (2.0 g, 10.5 mmol) in absolute EtOH (50 ml) were added acetic acid (1.85 g, 31.5 mmol), n-propylamine (1.85 g, 31.5 mmol) and 4 A molecular sieves. The mixture was refluxed for 3.5 h. The molecular sieves were filtered off and the solution was hydrogenated with 0.3 g PtO$_2$ in a Parr aparatus. The catalyst was filtered off (Celite) and the volatiles were evaporated. The resulting crude base was eluted through an SiO$_2$-column with methanol as eluant, affording an oil of 80% isomeric purity (GC). The hydrochloride was prepared and recrystallized two times from MeOH-ether. Yield 0.7 g (24%) of colourless cristals, m.p. 169°-171° C., isomeric purity (GC)>95%.

Example I5

(±)-cis-7-methoxy-1-methyl-2-(di-n-propylamino)tetralin (2)

NaBH$_4$ (0.41 g, 10.1 mmol) was added portionwise to a stirred solution of propionic acid (2.4 g, 32.5 mmol) in dry benzene (20 ml) under N$_2$, keeping the temperature below 20° C. After 2 h, compound 1 (0.5 g, 1.8 mmol) was added and the mixture was refluxed for 4 h and then treated with 10% Na$_2$CO$_3$ solution. The benzene layer was dried (Na$_2$SO$_4$) and the solvent was evaporated. The hydrochloride salt was prepared and recrystallized from MeOH-ether.

Yield 0.51 g (90%), m.p. 167°-168° C.

Example I6

(−)-cis-7-methoxy-1-methyl-2-(n-propylamino)tetralin (3)

Compound 1 x HCl (4.95 g, 18.3 mmol) in H$_2$O (100 ml) and CH$_2$Cl$_2$ (100 ml) was stirred at roomtemperature together with a solution of R(−)-O-methylmandelicacidchloride (3.37 g, 18.3 mmol) in CH$_2$Cl$_2$ (20 ml) and 100 ml 5% NaOH solution for 30 min. The organic layer was separated, washed with H$_2$O, dried (Na$_2$SO$_4$) and evaporated. The resulting oil (6.0 g) was chromatographed on a silica column with a 1:1-mixture of petroleumether: ether as eluant. Yield first diastereomer 2.0 g, the yield of the second diastereomer was 1.9 g. A solution of the first diastereomer (1.4 g, 3.5 mmol) in dry tetrahydrofurane (40 ml) was treated with 3.5 ml of a 2M hexane solution of normal butyllithium and a solution of ethylene oxide (0.2 ml) in dry tetrahydrofurane (10 ml). Evaporation of the volatiles gave an oil which was chromatographed on a silica column with methanol as eluant.

Yield 0.2 g of the pure base 3. The base was converted to the hydrochloride. m.p. 184°-204° C.; $[\alpha]_D^{25}$ −61.4, C 0.32 (MeOH). Example I7 (+)-cis-7-methoxy-1-methyl-2-(n-propylamino)tetralin (4)

A solution of the second diastereomer (1.4 g, 3.5 mmol) from experiment 3 in dry tetrahydrofurane (40 ml) was treated with 3.5 ml of a 2M hexane solution of normal butyllithium and a solution of ethyleneoxide (0.2 ml) in dry tetrahydrofurane (10 ml). Evaporation of the volatiles gave an oil which was chromatographed on a silica column with methanol as eluant. Yield 0.19 g of the pure base 4. The base was converted to the hydrochloride. m.p. 184°–207° C.; $[\alpha]_D^{25}$ +54.5, C 0.11 (MeOH).

Example I8
(−)-cis-7-methoxy-1-methyl-2-(di-n-propylamino)tetralin (5)

Compound 3 x HCl (0.2 g, 0.7 mmol) was reacted with NaBH$_4$ (0.2 g, 5.0 mmol) and propionic acid (1.2 g, 16.2 mmol) in benzene (10 ml) in the same fashion that for compound 2.
Yield 0.15 g (65%) m.p. 180°–183° C.

Example I9
(+)-cis-7-methoxy-1-methyl-2-(di-n-propylamino)tetralin (6)

Compound 4 x HCl (0.2 g, 0.7 mmol) was reacted with NaBH$_4$ (0.2 g, 5.0 mmol) and propionic acid (1.2 g, 16.2 mmol) in benzene (10 ml) in the same fashion that for compound 2.
Yield 0.15 g (65% m.p.: 178°–183° C.

Preparation of End Compounds

Example E 1.
cis-5-Hydroxy-1-methyl-2-(di-n-propylamino) tetralin hydrobromid cis-5-Methoxy-1-methyl-2-(di-n-propylamino)tetralin hydrochloride (150 mg, 0.48 mmol) was heated in 48% aqueous HBr for 2 h at 120° C. under N$_2$. The volatiles were evaporated in vacuo and the residue was applied to pre-coated PLC plates (silica gel 60 F$_{254}$, Merck) which were eluted with CHCl$_3$-MeOH (9:1). After elution of the product the volatiles were evaporated in vacuo and the residue was recrystallized at least twice. giving cis-hydroxy-1-methyl-2-(di-n-propyl-amino)tetralin.Hbr (66 mg, 48%) of an isomeric purity >95% (GC, 225° C.) IR (KBr) $\nu$3136 cm$^{-1}$ (O-H$_{str}$); NMR (MeOH-d$_4$), $\delta$1.05 (t,6H), $\delta$1.31 (d,3H), $\delta$1.50–3.74 (m,14H), $\delta$6.44–6.69 (m,2H), $\delta$6.81–7.07 (m,1H); MS (70 eV) m/z 261 (36%), 232 (100%), 161 (82%).

Example E2.
cis-7-Hydroxy-1-methyl-2-(di-n-propylamino) tetralin hydrobromide cis-7-Methoxy-1-methyl-2-(di-n-propylamino) tetralin hydrochloride (500 mg, 1.60 mmol) was heated in 48% aqueous HBr (5ml) for 3 h at 140° C. under N$_2$. Water (20 ml) was added and the volatiles were evaporated in vacuo. The faint orange-coloured residue was treated with abs. ethanol twice (with intervening evaporation). The dry residue was dissolved in methanol and the solution was treated with active charcoal. After filtration the solvent was evaporated, whereupon the residue was dissolved in methanol and ethyl ether was added. The obtained white crystals were recrystallized from MeOH-ethyl ether yielding the desired product (450 mg, 84% yield), m.p. 195°–196° C.

Example E3.
cis-7-hydroxy-1-methyl-2-(n-propylamino) tetralin hydrobromide cis-7-Methoxy-1-methyl-2-(n-propylamino) tetralin hydrochloride (100 mg, 0.37 mmol) was heated in 48% aqueous HBr for 3 h at 120° C. under N$_2$. The volatiles were evaporated from the faint pink solution and the residue was treated twice with ethanol followed by evaporation, giving a faint pink residue which was dissolved in abs. ethanol. Dry abs. ethyl ether was added to the solution, yielding white crystals which were then recrystallized from MeOH-ethyl ether, yielding the desired product (75 mg, 70% yield), m.p. 262°–263° C.

Example E4.
cis-1-ethyl-5-hydroxy-2-(di-n-propylamino) tetralin hydrobromide cis-1-Ethyl-5-methoxy-2-(di-n-propylamino) tetralin hydrochloride (150 mg, 0.46 mmol) was heated in 48% aqueous HBr for 2 h at 120° C. under N$_2$. The volatiles were evaporated in vacuo and the residue was crystallized from MeOH-ethyl ether. Two recrystallizations from MeOH-ethyl ether gave the desired product as HBr-salt (68 mg, 42%). Isomeric purity >95% (6C, 250° C.).

Example E5.
cis-5-1,N-Dimethyl-5-hydroxy-2-(n-propylamino)-tetralin hydrochloride A mixture of cis-5-methoxy-1-methyl-2-(n-propylamino)tetralin hydrochloride (200 mg; 0.67 mmol), 37% formalin (0.3 ml; 3.33 mmol), NaBH$_3$CN (140 mg; 2.23 mmol) and 3 Å molecular sieves (400 mg) in methanol (5 ml) wsa stirred (N$_2$) for 3 days at room temperature. The molecular sieves were filtered off and the solvent was evaporated. The residue was dissolved in 10% HCl and was extracted with CH$_2$Cl$_2$. The organic layer was dried (Na$_2$SO$_4$) and evaporated. The desired compound was recrystallized from ethanol/ether. Mp: 236°–238° C. MS(70 eV) m/z 233 (81%), 204 (100%), 161 (100%) Yield 200 mg; (95%).

Example E6.
cis-5-Hydroxy-N-(3-hydroxy-phenethyl)-1-methyl 2-(n-propylamino)tetralin hydrochloride NaBH$_4$ (210 mg; 5.55 mmol) was added portionwise to a solution of 3-methoxy-phenylacetic acid (3 g: 18 mmol) in dry benzene (15 ml). The temperature was kept below 15° C. After 2 hours a solution of cis-5-methoxy-1-methyl-2-(n-propylamino)tetralin (380 mg; 1.11 mmol) in dry benzene (15 ml) was added and the mixture was refluxed for 3 hours. The mixture was partitioned between 2M NaOH (20 ml) and ether. The organic layer was dried (K$_2$CO$_3$) and evaporated. The residual oily product was purified on a silica column eluated with ethyl acetate. NMR showed the desired intermediate product.
Yield 320 mg (72%) (CDCl$_3$), $\delta$0.90 (t, 3H), $\delta$1.18 (d, 3H), $\delta$3.80 (s, 6H), $\delta$3.4–0.6 (m, 10H), $\delta$6.83 (m, 5H), $\delta$7.20 (m, 2H).
The intermediate cis-5-methoxy-N-(3-methoxyphenethyl)-1-methyl-2-(n-propylamino)tetralin (320 mg, 0.79 mmol) was heated in aqueous 48% HBr (5 ml) for 2 hours at 120° C. under N$_2$. The mixture was evaporated and the residue was made alkaline with diluted NaHCO$_3$ and extracted 3 times with ether. After drying and evaporation the diphenolic base was converted to its hydrochloride. Yield 60 mg (17%) MMR (CDCl$_3$), $\delta$0.82 (1, 3H), $\delta$1.12 (d, 2H), $\delta$3.80-0.55 (m, 19H), $\delta$6.0 (s, 2H phenolic), $\delta$6.66 (m, 4H), $\delta$7.06 (m, 3H) MS (70 eV) m/z 339 (2%), 232 (100%), 161 (70%).

Example E7.
cis-1-Methyl-5-(4-pivaloyloxybenzoyloxy)-2-(di-n-propylamino) tetralin hydrochloride Cis-5-hydroxy-1-methyl-2-(di-n-propylamino) tetralin hydrobromide (500 mg; 1.46 mmol) was suspended in dry dichloromethane (4 ml). Pivaloyloxybenzoyl chloride (387 mg; 1.60 mmol) was dissolved in a mixture of dichloromethane (4 ml) and pyridine (127 mg; 1.60 mmol). The solution was added to the suspension and the mixture was refluxed for 20 hours. The clear solution was cooled, washed with aqueous NaHCO$_3$ and dried (Na$_2$SO$_4$). After evaporation the residual oil was purified on a silica column eluated with CH$_2$Cl$_2$-MeOH (90+10). The pure base was converted to its hydrochloride.

Yield 200 mg (27%).Mp: 128°-31° C. NMR (CDCl$_3$) δ0.83 (t, 6H), δ1.20 (d, 3H), δ1.36 (s, 9H), δ3.60-0.60 (m, 26H), δ7.13 (m, 3H), δ7.23 (d, 2H), δ8.30 (d, 2H). MS (70 eV) m/z 465 (23%), 436 (100%), 205 (45%), 121 (78%).

Example E8.
cis-N-Allyl-5-hydroxy-1-methyl-2-(n-propylamino)tetralin hydrochloride To a solution of cis-5-methoxy-1-methyl-2-(n-propylamino)tetralin (400 mg; 1.71 mmol) in CH$_3$CN (9 ml), solid K$_2$CO$_3$ (430 mg; 3.11 mmol) was added and then the mixture was refluxed. A solution of allylbromide (380 mg; 3.14 mmol) in CH$_3$CN (2 ml) was added dropwise during 30 minutes and then the mixture was refluxed for additional 30 minutes. The cooled solution as filtered off and the solvent evaporated giving a residual oil of the desired intermediate. The compounds was converted to its hydrochloride and was recrystallized from methanol/ether. Mp: 147°-149° C., Yield 280 mg (60%).

The intermediate cis-N-allyl-5-methoxy-1-methyl-2-(n-propylamino) tetralin hydrochloride (20 mg; 0.68 mmol) was dissolved in CHCl$_3$ (2 ml) and added during 2 minutes to a well-stirred solution of BBr$_3$ (1.10 g; 4.39 mmol) in CHCl$_3$ (13 ml) maintained in the temperature range 23°-26° C. The stirring was continued for 15 minutes at 20° C. The reaction mixture was poured into a well-stirred mixture of ice (6 g) and concentrated NH$_4$OH (1.5 ml). The two-phase system was kept at 0° for 30 minutes with continuous stirring. The system was separated and the organic phase was dried and evaporated. The desired oily product was precipitated as a hydrochloride salt and was recrystallized from CHCl$_3$/ether.

Yield: 100 mg (50%) NMR (CDCl$_3$), δ0.89 (t, 3H), δ1.20(d, 3H), δ3.53-0.60(m, 18H), δ4.96 (s, 1H phenolic), δ5.07 (m, 1H), δ5.31 (m, 1H), δ6.02 (m, 1H), δ6.70 (m, 2H), δ7.10 (m, 1H), MS (70 eV) m/z 259 (45%), 161 (100%) 124 (79%).

Example E9.
cis-5-Hydroxy-1-methyl-2-(N-n-pentyl-N-n-propylamino) tetralin hydrochloride cis-5-Methoxy-1-methyl-2-(N-n-pentyl-N-n-propylamino) tetralin hydrochloride (500 mg; 1.5 mmol) was heated in aqueous 48% HBr (3 ml) for 2 hours at 120° C. under N$_2$. The mixture was evaporated and the residue was made alkaline with diluted NaHCO$_3$ and extracted 3 times with ether. After drying (Na$_2$SO$_4$) and evaporation the product was precipitated as hydrochloride salt. Yield: 290 mg (60%) NMR (CDCl$_3$), δ0.86 (t, 6H) δ1.17 (d, 3H), δ3.23-0.60 (m, 27H) δ5.36 (s, 1H phenolic) δ6.90 (m, 3H), MS (70 eV) m/z 289 (33%), 161 (100%), 232 (82%).

Example E10.
cis-5-acetoxy-1-methyl-2-(di-n-propylamino) tetralin hydrochloride cis-5-Hydroxy-1-methyl-2-(di-n-propylamino) tetralin hydrobromide (600 mg; 1.8 mmol) was dissolved in acetic anhydride (10 ml). Triethylamine (0.5 ml) was added and the solution was refluxed for 1.5 hour. Ethanol (25 ml) was added and the solvents were evaporated giving a residual oil. The oil was made alkaline with diluted NaOH to pH 10 during external cooling and extracted with ether. The organic phase was dried and evaporated giving the desired compound as an oil. The hydrochloride salt was prepared with HCl-saturated ether in dry ether. Filtrations and drying gave the desired compound in crystalline form.

Yield 400 mg (67%). Mp 194°-194.5° C.

Example E 11.
(+)-cis-5-Hydoxy-1-methyl-2-(di-n-propylamino) tetralin hydrochloride (+)-cis-5-Methoxy-1-methyl-2-(n-propylamino)tetralin hydrochloride (0.29 g, 0.00093 mol) in 48% aqueous HBr (15 ml) was heated at 125° C. for 2 hours under N$_2$. The volatiles were removed in vacuo and the residue was alkalinized with saturated aqueous NaHCO$_3$ and the mixture was extracted several times with ether. The combined ether layers were dried (Na$_2$SO$_4$), filtered and HCl-saturated ether was added giving a precipitate which was recrystallized from ethanol-ether giving (+)-cis-5-hydroxy-1-methyl-2-(di-n-propylamino)tetralin hydrochloride (0.16 g, 58%) m.p. 228°-229° C., $[\alpha]_D^{22} = +49.8$ (c=1.1, CH$_3$OH).

Example E 12.
(-)-cis-5-Hydroxy-1-methyl-2-(di-n-propylamino)tetralin hydrochloride (-)-cis-5-Methoxy-1-methyl-2-(di-n-propylamino)tetralin hydrochloride (0.37 g, 0.0012 mol) was treated with 48% HBr (15 ml) as described above to give (-)-cis-5-hydroxy-1-methyl-2-(di-n-propylamino)tetralin hydrochloride (0.26 g, 55%) m.p. 228°-229° C., $[\alpha]_D^{22} = -50.1$ (c=1.1, CH$_3$OH).

Pharmaceutical Preparations

The following examples illustrate how the compounds of the present invention may be included into pharmaceutical preparations.

Example P 1. Preparation of soft gelatine capsules 500 g of active substance are mixed with 500 g of corn oil, whereupon the mixture is filled in soft gelatine capsules, each capsule containing 100 mg of the mixture (i.e. 50 mg of active substance).

Example P 2. Preparation of tablets 0.5 kg of active substance are mixed with 0.2 kg of silicic acid of the trade mark Aerosil. 0.45 kg of potato starch and 0.5 kg of lactose are mixed therewith and the mixture is moistened with a starch paste prepared from 50 g of potato starch and distilled water, whereupon the mixture is granulated through a sieves. The granulate is dried and sieved, whereupon 20 g of magnesium stearate are mixed into it. Finally the mixture is pressed into tablets each weighing 172 mg.

Example P 3. Preparation of a syrup 100 g of active substance are dissolved in 300 g of 95% ethanol, whereupon 300 g of glycerol, aroma and colouring agents (q.s.) and 1000 ml of water are mixed therein. A syrup is obtained.

Example P 4. Preparation of an injection solution

Active substance (hydrobromide) (1 g), sodiumchloride (0.8 g) and ascorbic acid (0.1 g) are dissolved in sufficient amount of distilled water to give 100 ml of solution. This solution, which contains 10 mg of active substance per ml, is used in filling ampoules, which are sterilized by heating at 120° C. for 20 minutes.

Pharmacological Evaluation

Drugs acting on central dopamine (DA) transmission have for long been known to be clinically effective in a variety of diseases originating in the CNS, e.g. parkinsonism and schizophrenia. In the former condition the nigro-neostriatal hypofunction can be restored by an increase in postsynaptic DA-receptor stimulation, whereas the latter condition can be normalized by achieving a decrease in postsynaptic DA-receptor stimulation. So far, this decrease has been mainly accomplished either by a) direct blockade of the postsynaptic DA receptors (considered to be the mode of action for classical antipsychotic agents like e.g. haloperidol and chlorpromazine) or b) inhibition of intraneuronal presynaptic events essential for the maintenance of adequate neurotransmission, e.g. granular uptake and storage (cf. the neuroleptic reserpine, which is known to deplete the monoamine stores via its actions upon granular structures), transport mechanism and transmitter synthesis.

In recent years a large body of pharmacological, biochemical and electrophysiological evidence has accumulated, providing considerably support in favour of the existence of a specific population of central autoregulatory DA receptors, so-called autoreceptors, located on the dopaminergic neuron itself (i.e. presynaptically located). These receptors are part of a homeostatic mechanism that modulates nerve impulse flow and transmitter synthesis and thus the amount of DA released from the nerve endings.

Direct DA-receptor agonists like e.g. apomorphine is able to activate the DA autoreceptors as well as the postsynaptic DA receptors. At low doses, however, the effects of autoreceptor stimulation appear to predominate, whereas at higher doses the (autoreceptor-mediated) attenuation of DA transmission is outweighed by the enhancement in postsynaptic receptor stimulation. Thus, the "paradoxical" antipsychotic and antidyskinetic effects demonstrated in man after low doses of apomorphine are most probably to be attributed to the autoreceptor-stimulatory properties of this DA-receptor agonist. In accordance with this, and in view of current knowledge of the drawbacks linked to the use of DA-receptor antagonists in the therapy of schizophrenia and other psychotic disorders, it has been suggested that DA-receptor stimulants with a high selectivity for CNS DA autoreceptors would offer new therapeutic principles of great value in psychiatric medicine. At the moment only one such drug (3-PPP; see below) is commonly known. While searching for new postsynaptic DA-receptor agonists (anti-Parkinson agents) we surprisingly discovered another group of substances possessing selective DA-autoreceptor agonistic properties. For compound numbers see table of "End Compound" above.

Pharmacological Procedures

1. Antagonism of the reserpine-induced "neuroleptic syndrome" in the rat.

Depletion of the monoamine stores with reserpine brings about a "neuroleptic syndrome" characterized by hypomotility, catalepsy, muscle rigidity, hunchbacked posture as well as a number of other central and peripheral signs of monoamine depletion. This syndrome can be reversed by the administration of drugs that stimulate postsynaptic DA receptors directly or indirectly, e.g. apomorphine and amphetamine. The effect of amphetamine is, however, dependent on an intact synthesis machinery and can be abolished by the additional pretreatment with α-methyl-para-tyrosine, an inhibitor of tyrosine hydroxylation (the rate-limiting step in the synthesis of DA).

Male Sprague-Dawley rats (150–300 g) were pretreated with reserpine and α-methyl-para-tyrosine and then given the compounds under evaluation in order to detect possible behavioural postsynaptic DA-receptor stimulating effects (for details; see lengend of table II).

A comparison of compound 2 (cis-1-CH$_3$-5-OH-DPAT) to the structurally related 5-hydroxy-2-(di-n-propylamino)tetralin (5-OH-DPAT) and trans-1-methyl-5-hydroxy-2-(di-n-propylamino)tetralin (trans-1-CH$_3$-5-OH-DPAT) clearly demonstrates that whereas 5-OH-DPAT and trans-1-CH$_3$-5-OH-DPAT both are efficient postsynaptic DA-receptor stimulants, compound 2 is not. This inability of compound 2 to antagonize the reserpine-induced syndrome is shared by the selective Da-autoreceptor agonist 3-PPP [3-(3-hydroxyphenyl)-N-n-propylpiperidine], thus markedly contrasting to the pronounced stereotyped and hyperactive behaviour that can be elicited by postsynaptic DA-receptor stimulating agents like apomorphine, 5-OH-DPAT and trans-1-CH$_3$-5-OH-DPAT.

2. Determination of rat-brain in-vivo tyrosine hydroxylation.

The compounds under evaluation were tested biochemically for central DA-receptor (pre- and/or postsynaptic) stimulating activity. The concept of this biochemical screening method is that a DA-receptor agonist will stimulate the receptor and through regulatory feedback systems effect a decline in tyrosine hydroxylase activity and thus a subsequent reduction in the synthesis rate for DA in the presynaptic neuron. Dopa formation, as determined after in-vivo inhibition of the aromatic L-amino acid decarboxylase with NSD 1015 (3-hydroxybenzyl-hydrazine hydrochloride), is taken as an indirect measure of DA synthesis rate.

Rats (150–300 g) pretreated with reserpine were given the compounds under evaluation. Gross behavioural observations (changes in motility, stereotypies etc.) were made in order to evaluate possible postsynaptic dopamine receptor activity. subsequent administration of NSD 1015, decapitation, brain dissection [corpora striata, limbic fore-brain and rest of the hemispheral parts (cortex)]homogenization, centrifugation, ion-exchange chromatography and spectro-fluorimetric measurements (all as described in detail by Wikstrom et al., in J. Med. Chem. 21, 864–867, 1978 and references cited therein), gave the actual Dopa levels.

Several doses (n=4–6) were tested in order to obtain dose-response curves for each compound and brain area. The dose of a compound producing a half-maximal decrease in the Dopa level in the rat brain part was then estimated. These values (ED$_{50}$) are presented in Table I. (Simultaneous determination of the 5-HTP levels was also performed utilizing the same paradigm.)

From studies on many other compounds having autoreceptor activity as well as postsynaptic activity we known that at a dose representing the ED$_{50}$ value only autoreceptor activation is likely to occur. To obtain postsynaptic activation higher doses are necessary. (At the moment no compound with selective postsynaptic DA-stimulating activity is known). Therefore, independently of other presented evidence (above or below) concerning receptor selectivity, the ED$_{50}$ values are considered to represent doses eliciting selective autoreceptor stimulation.

From the data in Table I it can be seen that all compounds tested are biochemically active except for the 1,1-di-CH$_3$-5-OH-DPAT and its monopropyl analogue (1,1-di-CH$_3$-5-OH-PAT) which are completely inactive even at 45 μmol/kg. Compound 2 is equipotent to trans-1-CH$_3$-5-OH-DPAT and, despite being less potent than 5-OH-DPAT, retains considerable potency and is of the same order of potency as apomorphine. Interestingly, compound 2 is approximately 5 times more potent than the previously described selective DA-autoreceptor agonist 3-PPP.

None of the compounds neither affect the Dopa accumulation in the cortical areas nor the 5-HTP accumulation in any rat brain part investigated, suggesting lack of noradrenaline and 5-HT-receptor stimulatory effects, respectively.

3. Effect on spontaneous locomotor activity and brain DA synthesis rate in the rat.

Untreated animals exposed to a new environment display an initial high motor activity which then gradually declines over a period of time. Administration of DA-receptor agonists (e.g. apomorphine) in doses where preferential autoreceptor stimulation is likely to occur, causes a depression of the spontaneous motility mentioned above, considered to be due to the DA autoreceptor-medicated attenuation of central DA transmission.

Rats (150–300 g) were injected subcutaneously with compound 2, 5-OH-DPAT or apomorphine and after 5 minutes they were individually placed in motility boxes ("M/P 40 Fc Electronic Motility Meter", Motron Products, Stockholm) and the motor activity (0–30 min) was quantified. Compound 2 exhibits a clear and significant dose-dependent decrease of the initial high motor activity, the maximal effect (being a 70% decrease from control values) attained at about 4 mg/kg. No locomotor stimulation is ever seen with compound 2, regardless of the dose used. These findings are in congruence with the results obtained with the selective DA-autoreceptor agonist 3-PPP [S. Hjorth t al., Life Sciences, 28, 1225 (1981)] but in sharp contrast to the results obtained with 5-OH-DPAT and apomorphine (Table III). Since the latter two compounds are able to stimulate the DA-autoreceptors (at low doses) as well as postsynaptic DA-receptors they give rise to the well-known biphasic dose-response pattern indicated in Table III; lower doses significantly suppressing and higher dosess significantly stimulating the rat locomotor activity.

The dose-dependent locomotor suppression produced by compound 2 is accompanied by a significant decrease in rate brain DA synthesis rate without any concomitant change in brain 5-HT synthesis rate (Tables IV-V). The marked difference in response between the limbic forebrain and the striatal structures (Table IV) is of considerable interest since it indicates but slight incidence of extrapyramidal side effects when used as a psychotherapeutic agent.

4. A Comparative study of compound 2, its trans-analogue, and some known dopaminergic agents Rats (150–300 g) pretreated with reserpine and α-methyl-paratyrosine were given compound 2, trans-1-CH$_3$-5-OH-DPAT, apomorphine, 3-PPP or saline subcutaneously (for experimental details see legend to Table II) and the locomotor activity (accumulated counts 0–60 min.) was quantified by means of motility meters (Motron; see under 3 above).

The results (Table II) show that, apart from their DA-autoreceptor actions (ED$_{50}$'s, cf. 2 above), trans-1-CH$_3$-5-OH-DPAT, 5-OH-DPAT as well as apomorphine exhibit strong central postsynaptic DA-receptor stimulatory effects. In contrast to the latter agonists, compound 2 appeared to selectively act on the DA autoreceptors and hence failed to elicit a motor response that differed more than slightly from control values. This suggestion is also further strengthened by the direct comparison with the previously known selective DA-autoreceptor agonist 3-PPP.

Conclusion

The pharmacological data affirm the hypothesis that the compounds under consideration are centrally acting selective DA autoreceptor stimulating agents, and thus of great clinical interest in the treatment of mental disorders such as schizophrenia and a number of other disease states such as tardive dyskinesia, Huntington's chorea, hypoprolactinemia, alcoholism and drug abuse, said mental disorders and other disease states possibly being associated with a disturbance in central DA transmission.

TABLE I

Biochemical data for compound 2 and analogues

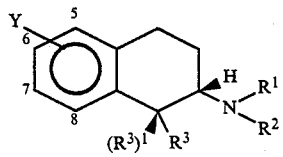

| Compound[a] | Y | R$^1$ | R$^2$ | R$^3$ | (R$^3$) | Salt | Dopa-accumulation; ED$_{50}$ (μmol/kg s.c.)[bc] Limbic | Striatum |
|---|---|---|---|---|---|---|---|---|
| cis-1-CH$_3$—5-OH—DPAT (2) | 5-OH | n-C$_3$H$_7$ | n-C$_3$H$_7$ | CH$_3$ | H | HBr | 0.67 | 0.80 |

TABLE I-continued

Biochemical data for compound 2 and analogues

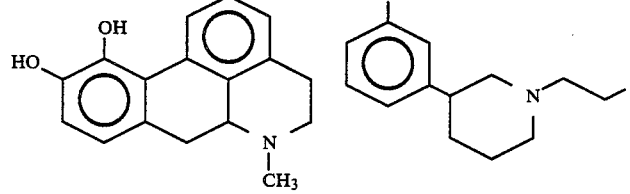

| Compound[a] | Y | R[1] | R[2] | R[3] | (R[3]) | Salt | Dopa-accumulation; $ED_{50}$ ($\mu$mol/kg s.c.)[b,c] Limbic | Striatum |
|---|---|---|---|---|---|---|---|---|
| trans-1-CH₃—5-OH—DPAT | 5-OH | n-C₃H₇ | n-C₃H₇ | H | CH₃ | HBr | 0.66 | 0.73 |
| 1,1-di-CH₃—5-OH—DPAT | 5-OH | n-C₃H₇ | n-C₃H₇ | CH₃ | CH₃ | HBr | I[d] | I |
| 1,1-di-CH₃—5-OH—PAT | 5-OH | n-C₃H₇ | H CH₃ | CH₃ | | HBr | I | I |
| 5-OH—DPAT | 5-OH | n-C₃H₇ | n-C₃H₇ | H | H | HBr | 0.111[e] | 0.009[e] |
| Apomorphine | | | | | | HCl | 0.19[e] | 0.22[e] |
| 3-PPP | | | | | | HBr | 3.6 | 3.6 |

[a]Abbreviations used in the table: cis-1-CH₃—5-OH—DPAT = cis-1-CH₃—5-OH—2-(dt-n-propylamino)tetralin; trans-1-CH₃—5-OH—DPAT = trans-1-CH₃—5-OH—2-(di-n-propylamino)tetralin; 1,1-di-CH₃—5-OH—DPAT = 1,1-di-CH₃—5-OH—2-(di-n-propylamino) tetralin; 1,1-di-CH₃—5-OH—PAT = 1,1-di-CH₃—5-OH—2-(n-propylamino)tetralin; 5-OH—DPAT = 5-OH—2(2-n-propylamino)tetralin; 3-PPP = 3-(3-hydroxyphenyl)- N—n-propylpiperidine.
[b]Rats pretreated with reserpine (10 mg/kg i.p.; 18 h) were given the compounds under evaluation. Fortyfive minutes later they were injected with NSD 1015 (100 mg/kg i.p.) and after a further 30 min they were decapitated, the brains rapidly dissected and taken for determination of the Dopa and 5-HTP levels in different areas of the brain. The dose of a compound producing a half-maximal decrease ($ED_{50}$) in the Dopa level in the rat brain part was then estimated from dose-response curves comprising 4–6 dose levels. (For further details see the text and references).
[c]No effects upon the Dopa levels in the hemispheral (cortical) parts or upon the 5-HTP levels in any brain part investigated could be detected.
[d]I = Inactive. $ED_{50} > 45$ $\mu$mol/kg.
[e]Taken from Hacksell et al., J. Med. Chem. 22, 1469 (1979).

TABLE II

Antagonism of the reserpine plus α-methyl-para-tyrosine-induced immobility in rats

| Compound | Dose (mg/kg s.c.) | Motor activity (counts 0–60 min) | n |
|---|---|---|---|
| cis-1-CH₃—5-OH—DPAT (2) | 10 | 52 ± 5 | 3 |
| trans-1-CH₃—5-OH—DPAT | 10 | 406 ± 47 | 4 |
| 5-OH—DPAT | 0.75 | 620 ± 20 | 4 |
| Apomorphine | 1 | 517 ± 56 | 4 |
| 3-PPP | 10 | 51 ± 19 | 4 |
| 0.9% Saline | | 11 ± 4 | 4 |

Rats were given reserpine (10 mg/kg i.p.) and α-methyl-para-tyrosine (an inhibitor of tyrosine hydroxylase; 250 mg/kg i.p.) 6 and 1 h, respectively, prior to injection with compound 2 (10 mg/kg s.c.), trans-1-CH₃—5-OH—D-PAT (10 mg/kg s.c.), 5-OH—DPAT (0.75 mg/kg s.c.), apomorphine (1 mg/kg s.c.), 3-PPP (10 mg/kg s.c.) or saline. (For explanation of the abbreviations used, see legend of table 1). Immediately thereafter the animals were placed individually in the motility boxes and their motor activity was followed and recorded during the subsequent 60 minutes. Shown are the means ± s.e.m.

TABLE III

Comparison of the effects of compound 2, 5-OH—DPAT and apomorphine upon the locomotor activity in non-pretreated rats.

| Compound | Dose; mg/kg s.c. | Locomotor activity; counts 0.30 min | n | Statistical difference from (Anova followed by t-test) |
|---|---|---|---|---|
| 2 | 0 | 214 ± 25 | 10 | |
| | 0.0625 | 146 ± 4 | 4 | $p < 0.025$ |
| | 0.25 | 117 ± 11 | 7 | $p < 0.001$ |
| | 1.0 | 82 ± 8 | 7 | $p < 0.001$ |
| | 4.0 | 62 ± 5 | 5 | $p < 0.001$ |
| | 16.0 | 63 ± 9 | 5 | $p < 0.001$ |
| 5-OH—DPAT | 0 | 214 ± 25 | 10 | |
| | 0.0125 | 84 ± 11 | 3 | $p < 0.025$ |
| | 0.05 | 380 ± 24 | 3 | $p < 0.005$ |
| Apomorphine | 0 | 211 ± 24 | 6 | |
| | 0.1 | 134 ± 9 | 6 | $p < 0.025$ |

TABLE III-continued

Comparison of the effects of compound 2, 5-OH—DPAT and apomorphine upon the locomotor activity in non-pretreated rats.

| Compound | Dose; mg/kg s.c. | Locomotor activity; counts 0.30 min | n | Statistical difference from (Anova followed by t-test) |
|---|---|---|---|---|
| | 1.0 | 439 ± 67 | 6 | $p < 0.01$ |

Non-pretreated rats were given compound 2 (0.0625–16.0 mg/kg), 5-OH—2-(di-n-propylamino) tetralin (5-OH—DPAT; 0.0125–0.05 mg/kg, apomorphine (0.1–1.0 mg/kg) or saline subcutaneously. Five minutes later they were placed individually into motility meters and the locomotor activity was followed and recorded during the subsequent 30 min. Immediately thereafter the animals were removed from the boxes. Part of the animals were injected with NSD 1015 (100 mg/kg i.p.) and after a further 30 min they were killed, the brains rapidly dissected and taken for determination of the Dopa and 5-HTP levels in different areas of the brain. The results from these biochemical analyses are presented in table IV and V.

TABLE V

Effect of various doses of compound 2 on the formation of 5-hydroxytryptophan in rat brain regions. For experimental details see table III

| Compound 2 Dose; mg/kg s.c. | | Limbic forebrain | Striatum | Hemispheral (cortical) parts | Dien- cephalon | Brain- stem |
|---|---|---|---|---|---|---|
| 0 | mean | 357 ± 8 | 492 ± 7 | 56 ± 3 | 212 ± 12 | 115 ± 4 |
| | sem n | 6 | 6 | 6 | 5 | 6 |
| 0.0625 | | 314 ± 15 | 458 ± 17 | 40 ± 3 | 196 ± 8 | 98 ± 4 |
| | | 4 | 4 | 4 | 4 | 4 |
| | | $p < 0.025$ | n.s. | $p < 0.001$ | n.s. | n.s. |
| 0.25 | | 305 ± 14 | 448 ± 26 | 46 ± 2 | 170 ± 9 | 96 ± 11 |
| | | 3 | 4 | 4 | 4 | 4 |
| | | $p < 0.025$ | n.s. | $p < 0.025$ | $p < 0.025$ | n.s. |
| 1.0 | | 291 ± 9 | 420 ± 30 | 43 ± 3 | 170 ± 11 | 96 ± 7 |
| | | 4 | 4 | 4 | 4 | 4 |
| | | $p < 0.005$ | $p < 0.025$* | $p < 0.005$ | $p < 0.025$ | n.s. |
| 4.0 | | 267 ± 6 | 479 ± 9 | 47 ± 2 | 176 ± 10 | 111 ± 8 |
| | | 5 | 5 | 5 | 5 | 5 |
| | | $p < 0.001$ | n.s. | $p < 0.025$ | $p < 0.025$ | n.s. |
| 16.0 | | 272 ± 20 | 478 ± 10 | 48 ± 3 | 214 ± 13 | 118 ± 4 |
| | | 5 | 5 | 5 | 5 | 5 |
| | | $p < 0.001$ | n.s. | $p < 0.05$ | n.s. | n.s. |

*t-test vs. control(in all other cases Anova followed by t-test).
n.s. = not significant

TABLE IV

Effect of various doses of compound 2 on the formation of Dopa in rat brain regions. For experimental details see table III.

| Compound 2 Dose; mg/kg s.c. | | Limbic forebrain | Striatum | Hemispheral (cortical) parts | Dien- cephalon | Brain- stem |
|---|---|---|---|---|---|---|
| 0 | mean | 114 ± 2 | 76 ± 4 | 65 ± 1 | 137 ± 4 | 184 ± 5 |
| | sem n | 6 | 6 | 6 | 5 | 6 |
| 0.0625 | | 114 ± 6 | 65 ± 4 | 66 ± 2 | 148 ± 5 | 177 ± 10 |
| | | 4 | 4 | 4 | 4 | 3 |
| | | n.s. | n.s. | n.s. | n.s. | n.s. |
| 0.25 | | 116 ± 3 | 71 ± 5 | 63 ± 2 | 144 ± 2 | 170 ± 6 |
| | | 4 | 4 | 4 | 4 | 4 |
| | | n.s. | n.s. | n.s. | n.s. | n.s. |
| 1.0 | | 107 ± 5 | 75 ± 6 | 60 ± 1 | 134 ± 7 | 167 ± 8 |
| | | 4 | 4 | 4 | 4 | 4 |
| | | n.s. | n.s. | $p < 0.05$ | n.s. | n.s. |
| 4.0 | | 113 ± 3 | 72 ± 4 | 59 ± 2 | 137 ± 3 | 170 ± 5 |
| | | 5 | 5 | 5 | 5 | 5 |
| | | n.s. | n.s. | $p < 0.025$ | n.s. | n.s. |
| 16.0 | | 108 ± 5 | 73 ± 4 | 59 ± 2 | 137 ± 5 | 170 ± 8 |
| | | 5 | 5 | 5 | 5 | 5 |
| | | n.s. | n.s. | $p < 0.025$ | n.s. | n.s. |

Anova followed by t-test
n.s. = not significant

Best mode of carrying out the invention

The compound cis-5-hydroxy-1-methyl-2-(di-n-propylamino) tetralin and its salts, processes for preparing said compound and methods of employing said compound in therapy, in particular for treatment of schizophrenia, represent the best mode of carrying out the invention known at present.

We claim:
1. A compound of the formula

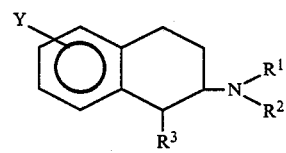

I wherein $R^3$ the $NR^1R^2$ group are in a cis-position to each other and wherein Y is in position 5 and is OH, or $R^6O$, whereby and $R^6$ is an allyl or benzyl group; $R^1$ is hydrogen or an alkyl group having 1-3 carbon atoms; $R^2$ is an alkyl group having 1-6 carbon atoms, a phenylalkyl- or m-hydroxyphenylalkyl group with 2-4 carbon atoms in the alkyl part, or an alkenyl group with 3-6 carbon atoms other than 1-alkenyl, and $R^3$ is an alkyl group having 1-3 carbon atoms, as the base or a pharmaceutically acceptable acid addition salt thereof.

2. A compound according to claim 1 wherein $R^6$ is an allyl group, and $R^1$, $R^2$ and $R^3$ have the meaning specified in claim 1.

3. A compound according to claim 1 wherein $R^6$ is allyl, $R^1$ is hydrogen or alkyl having 1-3 carbon atoms, $R^2$ is alkyl having 3-6 carbon atoms or a phenylalkyl or m-hydroxyphenylalkyl group hving an alkyl group with 2-3 carbon atoms, and $R^3$ is methyl or ethyl.

4. A compound according to claim 1 wherein $R^1$ is n-propyl.

5. A compound according to claim 4 wherein $R^2$ is an alkyl group having 3-6 carbon atoms or a phenylalkyl group with a straight alkyl group having 2-3 carbon atoms, and $R^3$ is methyl or ethyl.

6. A compound according to claim 1 wherein $R^3$ is methyl.

7. A compound according to claim 1 wherein Y is OH and is in 5 position.

8. The compound cis-5-hydroxy-1-methyl-2-(di-n-propylamino)tetralin.

9. A pharmaceutical preparation comprising as an active ingredient a compound according to claim 1, in conjunction with a pharmaceutically acceptable carrier.

10. A pharmaceutical preparation comprising as an active ingredient a compound according to claim 2, in conjunctio with a pharmaceutically acceptable carrier.

11. A pharmaceutical preparation comprising as an active ingredient a compound according to claim 3, in conjunction with a pharmaceutically acceptable carrier.

12. A pharmaceutical preparation comprising as an active ingredient a compound according to claim 4, in conjunction with a pharmaceutically acceptable carrier.

13. A pharmaceutical preparation comprising as an active ingredient a compound according to claim 5, in conjunction with a pharmaceutically acceptable carrier.

14. A pharmaceutical preparation comprising as an active ingredient a compound according to claim 6, in conjunction with a pharmaceutically acceptable carrier.

15. A pharmaceutical preparation comprising as an active ingredient a compound according to claim 9, in conjunction with a pharmaceutically acceptable carrier.

16. A pharmaceutical preparation comprising as an active ingredient cis-5-hydroxy-1-methyl-2-(di-n-propylamino)tetralin, in conjunction with a pharmaceutically acceptable carrier.

17. A method of treatment of disorders in the central nervous system, comprising administering to a host in need of treatment a therapeuticallly effective amount of a compound according to claim 1.

18. A compound of the formula

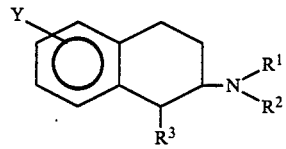

wherein $R^3$ and the $NR^1R^2$ group are in a cis-position to each other and wherein Y is in position 5 and is an alkoxy group containing 1-5 carbon atoms or a benzyloxy group; $R^1$ is hydrogen or an alkyl group having 1-3 carbon atoms; $R^2$ is an alkyl group having 1-6 carbon atoms, a phenylalkyl- or m-hydroxyphenylalkyl group with 2-4 carbon atoms in the alkyl part, or an alkenyl group with 3-6 carbon atoms other than 1-alkenyl; and $R^3$ is an alkyl group having 1-3 carbon atoms; or acid addition salts thereof.

19. A compound according to claim 18, wherein Y is —$OCH_3$ in the 5 position, $R^1$ and $R^2$ are n-propyl, and $R^3$ is methyl, said compound having a (—)-cis configuration.

20. A pharmaceutical preparation comprising as an active ingredient a compound according to claim 19, in conjunction with a pharmaceutically acceptable carrier.

21. A compound according to claim 7, wherein $R^3$ is methyl.

22. A compound according to claim 21, wherein $R^1$ and $R^2$ are both methyl or both ethyl.

23. A compound according to claim 22, wherein the compound has a (—)-cis configuration.

24. A compound according to claim 21, wherein $R^1$ is H and $R^2$ is n-propyl.

25. A compound according to claim 24, wherein the compound has a (—)-cis configuration.

* * * * *

UNITED STATES PATENT AND TRADEMARK OFFICE
CERTIFICATE OF CORRECTION

PATENT NO. : 4,876,284
DATED : Oct. 24, 1989
INVENTOR(S) : Arvidsson et al.

It is certified that error appears in the above-identified patent and that said Letters Patent is hereby corrected as shown below:

Title page, Item 75, 2nd line, "Gothenburg" should read --Göteborg--; 4th line, "Gothenborg" should read --Göteborg--; line 6, after "Askim," insert --John L. G. Nilsson, Tullinge; Domingo Sanchez, Floda; Håkan V. Wikström, Partille,--; Item 73, 2nd line, "Gothenburg" should read --Göteborg--; Item 63, 3rd line, "continuation" should read --continuation in part--; Item 56, 3rd line, "Seiles" should read --Seiler--; Item 56, following last line, insert:

--N-Alkylated 2-Aminotetralins: Central Dopamine-Receptor Stimulating Activity, Hacksell et al., Journal of Medicinal Chemistry, 1979, Vol. 22, No. 12, pp. 1469-1475

--Synthesis and Pharmacology of Some-2-Aminotetralins, Dopamine Receptor Agonists, John D. McDermed, Gerald M. McKenzie, and Arthur P. Phillips, Journal of Medicinal Chemistry, 1975, Vol. 18, No. 4, pp. 362-367

--Synthesis and Dopaminergic Activity of (±)-, (+)-, and (-)-2-Dipropylamino-5-hydroxy-1,2,3,4-tetrahydronaphthalene[1], John D. McDermed, Gerald M. McKenzie, and Harold S. Freeman, Journal of Medicinal Chemistry, 1976, Vol. 19, No. 4, pp. 547-549--.

Col. 2, line 20, "boradest" should read --broadest--. Col. 8, line 40, " 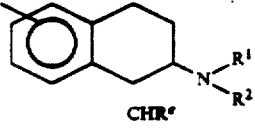 " should read -- 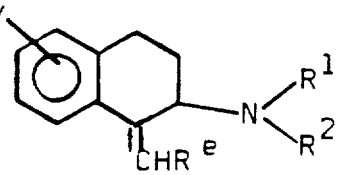 --.

Col. 10, line 30, that portion of the formula reading "Y" should read --$Y^1$-- and the numeral "I" at the righthand margin should be deleted; line 39, "method" should read --methods--. Col. 11, line 56, "metoxy" should read --methoxy--; line 59, "4 A" should

UNITED STATES PATENT AND TRADEMARK OFFICE
CERTIFICATE OF CORRECTION

PATENT NO. : 4,876,284
DATED : Oct. 24, 1989
INVENTOR(S) : Arvidsson et al.

It is certified that error appears in the above-identified patent and that said Letters Patent is hereby corrected as shown below:

read --4 Å--. Col. 13, line 21, "($K_2C_3$)" should read --($K_2CO_3$)--. Col. 14, line 3, "Examle" should read --Example--; line 10, "4 A" should read --4 Å--; line 13, "aparatus" should read --apparatus--; line 19, "cristals" should read --crystals--; line 59, "Example 17 ..." should be the beginning of a new heading on a separate line. Col. 15, line 20, "(65%" should read --(65%)--. Col. 16, line 57, "MMR" should read --NMR--. Col. 17, line 28, "as" should read --was--; line 29, "compounds" should read --compound--; line 35, "20 mg" should read --200 mg--. Col. 18, line 21, "Hydoxy" should read --Hydroxy--; line 65, "sieves" should read --sieve--. Col. 19, line 38, "considerably" should read --considerable--. Col. 20, line 34, "Da-autoreceptor" should read --DA-autoreceptor--. Col. 21, lines 40-41, "autoreceptor-medicated" should read --autoreceptor-mediated--. Col. 22, line 2, "t al." should read --et al.--; line 9, "dosess" should read --doses--; line 13, "rate" should read --rat--; 4th-from-bottom line, "bc" should read --b)c)--; 3rd-from-bottom line, "($R^3$)" should read --$(R^3)^1$--. Col. 23, line 6, "bc" should read --b)c)--; line 7, "($R^3$)" should read --$(R^3)^1$--; line 11, under col. $R^2$, "$\overline{H\ CH_3}$" should read --H--; under col. $(R^3)^1$, "HBr" should read --$CH_3$--; under col. Salt, "I" should read --HBr--; under col. Striatum, insert --I--; TABLE 1, 3rd line of footnote a, "2(2-n-propylamino)" should read --2(di-n-propylamino); TABLE III, following line 3, insert --the appropriate control groups--. Col. 25, following line 4 (and under "Statistical difference from", insert --the appropriate control groups--.

UNITED STATES PATENT AND TRADEMARK OFFICE
CERTIFICATE OF CORRECTION

PATENT NO. : 4,876,284

DATED : Oct. 24, 1989

INVENTOR(S) : Arvidsson et al.

It is certified that error appears in the above-identified patent and that said Letters Patent is hereby corrected as shown below:  "

<u>Col. 25,</u>

" TABLE V

Effect of various doses of compound 2 on the formation of 5-hydroxytryptophan in rat brain regions. For experimental details see table III

| Compound 2 Dose: mg/kg s.c. | | Limbic forebrain | Striatum | Hemispheral (cortical) parts | Diencephalon | Brainstem |
|---|---|---|---|---|---|---|
| 0 | mean sem n | 357 ± 8 6 | 492 ± 7 6 | 56 ± 3 6 | 212 ± 12 5 | 115 ± 4 6 |
| 0.0625 | | 314 ± 15 4 p < 0.025 | 458 ± 17 4 n.s. | 40 ± 3 4 p < 0.001 | 196 ± 8 4 n.s. | 98 ± 4 4 n.s. |
| 0.25 | | 305 ± 14 3 p < 0.025 | 448 ± 26 4 n.s. | 46 ± 2 4 p < 0.025 | 170 ± 9 4 p < 0.025 | 96 ± 11 4 n.s. |
| 1.0 | | 291 ± 9 4 p < 0.005 | 420 ± 30 4 p < 0.025* | 43 ± 3 4 p < 0.005 | 170 ± 11 4 p < 0.025 | 96 ± 7 4 n.s. |
| 4.0 | | 267 ± 6 5 p < 0.001 | 479 ± 9 5 n.s. | 47 ± 2 5 p < 0.025 | 176 ± 10 5 p < 0.025 | 111 ± 8 5 n.s. |
| 16.0 | | 272 ± 20 5 p < 0.001 | 478 ± 10 5 n.s. | 48 ± 3 5 p < 0.05 | 214 ± 13 5 n.s. | 118 ± 4 5 n.s. |

*t-test vs. control(in all other cases Anova followed by t-test).
n.s. = not significant

TABLE IV

Effect of various doses of compound 2 on the formation of Dopa in rat brain regions. For experimental details see table III.

| Compound 2 Dose: mg/kg s.c. | | Limbic forebrain | Striatum | Hemispheral (cortical) parts | Diencephalon | Brainstem |
|---|---|---|---|---|---|---|
| 0 | mean sem n | 114 ± 2 6 | 76 ± 4 6 | 65 ± 1 6 | 137 ± 4 5 | 184 ± 5 6 |
| 0.0625 | | 114 ± 6 4 n.s. | 65 ± 4 4 n.s. | 66 ± 2 4 n.s. | 148 ± 5 4 n.s. | 177 ± 10 3 n.s. |
| 0.25 | | 116 ± 3 4 n.s. | 71 ± 5 4 n.s. | 63 ± 2 4 n.s. | 144 ± 2 4 n.s. | 170 ± 6 4 n.s. |
| 1.0 | | 107 ± 5 4 n.s. | 75 ± 6 4 n.s. | 60 ± 1 4 p < 0.05 | 134 ± 7 4 n.s. | 167 ± 8 4 n.s. |
| 4.0 | | 113 ± 3 5 n.s. | 72 ± 4 5 n.s. | 59 ± 2 5 p < 0.025 | 137 ± 3 5 n.s. | 170 ± 5 5 n.s. |
| 16.0 | | 108 ± 5 5 n.s. | 73 ± 4 5 n.s. | 59 ± 2 5 p < 0.025 | 137 ± 5 5 n.s. | 170 ± 8 5 n.s. |

Anova followed by t-test
n.s. = not significant

UNITED STATES PATENT AND TRADEMARK OFFICE
CERTIFICATE OF CORRECTION

PATENT NO. : 4,876,284

DATED : Oct. 24, 1989

INVENTOR(S) : Arvidsson et al.

It is certified that error appears in the above-identified patent and that said Letters Patent is hereby corrected as shown below:

should read

--

Table IV. Effect of various doses of compound 2 on the formation of Dopa in rat brain regions. For experimental details see table III.

| Compound 2 Dose; mg/kg s.c. | | Limbic forebrain | Striatum | Hemispheral (cortical) parts | Diencephalon | Brainstem |
|---|---|---|---|---|---|---|
| 0 | mean<br>sem<br>n | 114<br>± 2<br>6 | 76<br>± 4<br>6 | 65<br>± 1<br>6 | 137<br>± 4<br>5 | 184<br>± 5<br>6 |
| 0.0625 | | 114<br>± 6<br>4<br>n.s. | 65<br>± 4<br>4<br>n.s. | 66<br>± 2<br>4<br>n.s. | 148<br>± 5<br>4<br>n.s. | 177<br>± 10<br>3<br>n.s. |
| 0.25 | | 116<br>± 3<br>4<br>n.s. | 71<br>± 5<br>4<br>n.s. | 63<br>± 2<br>4<br>n.s. | 144<br>± 2<br>4<br>n.s. | 170<br>± 6<br>4<br>n.s. |
| 1.0 | | 107<br>± 5<br>4<br>n.s. | 75<br>± 6<br>4<br>n.s. | 60<br>± 1<br>4<br>$p < 0.05$ | 134<br>± 7<br>4<br>n.s. | 167<br>± 8<br>4<br>n.s. |
| 4.0 | | 113<br>± 3<br>5<br>n.s. | 72<br>± 4<br>5<br>n.s. | 59<br>± 2<br>5<br>$p < 0.025$ | 137<br>± 3<br>5<br>n.s. | 170<br>± 5<br>5<br>n.s. |
| 16.0 | | 108<br>± 5<br>5<br>n.s. | 73<br>± 4<br>5<br>n.s. | 59<br>± 2<br>5<br>$p < 0.025$ | 137<br>± 5<br>5<br>n.s. | 170<br>± 8<br>5<br>n.s. |

Anova followed by t-test n.s. = not significant

UNITED STATES PATENT AND TRADEMARK OFFICE
CERTIFICATE OF CORRECTION

PATENT NO. : 4,876,284
DATED : Oct. 24, 1989
INVENTOR(S) : Arvidsson et al.

It is certified that error appears in the above-identified patent and that said Letters Patent is hereby corrected as shown below:

-- Table V. Effect of various doses of compound 2 on the formation of 5-hydroxytryptophan in rat brain regions. For experimental details see table III

| Compound 2 Dose; mg/kg s.c. | | Limbic forebrain | Striatum | Hemispheral (cortical) parts | Diencephalon | Brainstem |
|---|---|---|---|---|---|---|
| 0 | mean<br>sem ±<br>n | 357<br>8<br>6 | 492<br>± 7<br>6 | 56<br>± 3<br>6 | 212<br>± 12<br>5 | 115<br>± 4<br>6 |
| 0.0625 | | 314<br>± 15<br>4<br>$p < 0.025$ | 458<br>± 17<br>4<br>n.s. | 40<br>± 3<br>4<br>$p < 0.001$ | 196<br>± 8<br>4<br>n.s. | 98<br>± 4<br>4<br>n.s. |
| 0.25 | | 305<br>± 14<br>3<br>$p < 0.025$ | 448<br>± 26<br>4<br>n.s. | 46<br>± 2<br>4<br>$p < 0.025$ | 170<br>± 9<br>4<br>$p < 0.025$ | 96<br>± 11<br>4<br>n.s. |
| 1.0 | | 291<br>± 9<br>4<br>$p < 0.005$ | 420<br>± 30<br>4<br>$p < 0.025$* | 43<br>± 3<br>4<br>$p < 0.005$ | 170<br>± 11<br>4<br>$p < 0.025$ | 96<br>± 7<br>4<br>n.s. |
| 4.0 | | 267<br>± 6<br>5<br>$p < 0.001$ | 479<br>± 9<br>5<br>n.s. | 47<br>± 2<br>5<br>$p < 0.025$ | 176<br>± 10<br>5<br>$p < 0.025$ | 111<br>± 8<br>5<br>n.s. |
| 16.0 | | 272<br>± 20<br>5<br>$p < 0.001$ | 478<br>± 10<br>5<br>n.s. | 48<br>± 3<br>5<br>$p < 0.05$ | 214<br>± 13<br>5<br>n.s. | 118<br>± 4<br>5<br>n.s. |

* t-test vs. control (in all other cases Anova followed by t-test).

n.s. = not significant

UNITED STATES PATENT AND TRADEMARK OFFICE
CERTIFICATE OF CORRECTION

PATENT NO. : 4,876,284

DATED : Oct. 24, 1989

INVENTOR(S) : Arvidsson et al.

It is certified that error appears in the above-identified patent and that said Letters Patent is hereby corrected as shown below:

Col. 26, line 66, after "$R^3$" insert --and--; line 68, after "whereby" delete "and". Col. 27, line 15, "hving" should read --having--; line 26, "5 position" should read --5-position--; line 34, "conjunctio" should read --conjunction--. Col. 28, line 2, "claim 9" should read --claim 7--.

Signed and Sealed this

Seventeenth Day of March, 1992

Attest:

HARRY F. MANBECK, JR.

Attesting Officer

Commissioner of Patents and Trademarks